US011375601B2

(12) United States Patent
Trail et al.

(10) Patent No.: US 11,375,601 B2
(45) Date of Patent: Jun. 28, 2022

(54) FIELD REPLACEABLE, DISPOSABLE, AND THERMALLY OPTIMIZED X-RAY TARGET WITH INTEGRAL BEAM CURRENT MONITORING

(71) Applicant: ACCURAY INCORPORATED, Sunnyvale, CA (US)

(72) Inventors: Mark Trail, Sunnyvale, CA (US); Kirk Bertsche, Sunnyvale, CA (US); Douglas Bourne, Sunnyvale, CA (US)

(73) Assignee: ACCURAY INCORPORATED, Sunnyvale, CA (US)

(*) Notice: Subject to any disclaimer, the term of this patent is extended or adjusted under 35 U.S.C. 154(b) by 31 days.

(21) Appl. No.: 16/939,836

(22) Filed: Jul. 27, 2020

(65) Prior Publication Data
US 2022/0030695 A1 Jan. 27, 2022

(51) Int. Cl.
*H05G 2/00* (2006.01)
*H01J 35/18* (2006.01)
*G21K 5/00* (2006.01)
*A61N 5/00* (2006.01)

(52) U.S. Cl.
CPC ............. *H05G 2/00* (2013.01); *G21K 5/00* (2013.01); *H01J 35/186* (2019.05); *A61N 2005/005* (2013.01)

(58) Field of Classification Search
CPC .......... H05G 2/00; G21K 5/00; H01J 35/186; A61N 2005/005
See application file for complete search history.

(56) References Cited

U.S. PATENT DOCUMENTS

| 5,420,905 | A  | * | 5/1995  | Bertozzi | ........ | G01N 23/20091 |
|           |    |   |         |          |          | 378/86        |
| 2003/0058992 | A1 | * | 3/2003  | Marziale | .................. | H01J 3/02 |
|           |    |   |         |          |          | 378/65        |
| 2003/0147501 | A1 | * | 8/2003  | Geitz    | ..................... | H01J 35/13 |
|           |    |   |         |          |          | 378/142       |
| 2007/0248214 | A1 | * | 10/2007 | Smith    | ................. | A61N 5/1048 |
|           |    |   |         |          |          | 378/109       |

(Continued)

FOREIGN PATENT DOCUMENTS

| CN | 108578913 A | * | 9/2018  |
| DE | 1046789 B   |   | 12/1958 |
| JP | 2002054621 A | * | 2/2002 |

OTHER PUBLICATIONS

Transmittal of the International Search Report and Written Opinion of the International Searching Authority dated Nov. 19, 2021, for International Application No. PCT/US2021/039536, filed Jun. 29, 2021, pp. 18.

*Primary Examiner* — Chih-Cheng Kao
(74) *Attorney, Agent, or Firm* — Womble Bond Dickinson (US) LLP

(57) ABSTRACT

A linear accelerator target apparatus includes a target material to produce radiation upon being struck by electrons accelerated by a linear accelerator and a target holder assembly to which the target material is attached. The target holder assembly includes a cooling channel disposed around a perimeter of the target material. The target holder assembly is configured to be detachably coupled to a housing of the linear accelerator. The target apparatus further includes a protective window coupled to the target holder assembly over the target material.

20 Claims, 8 Drawing Sheets

(56) References Cited

U.S. PATENT DOCUMENTS

2010/0202593 A1\* 8/2010 Spence ............... A61B 6/4488
378/204
2011/0051899 A1\* 3/2011 Schumacher ........... H05G 2/00
378/123

\* cited by examiner

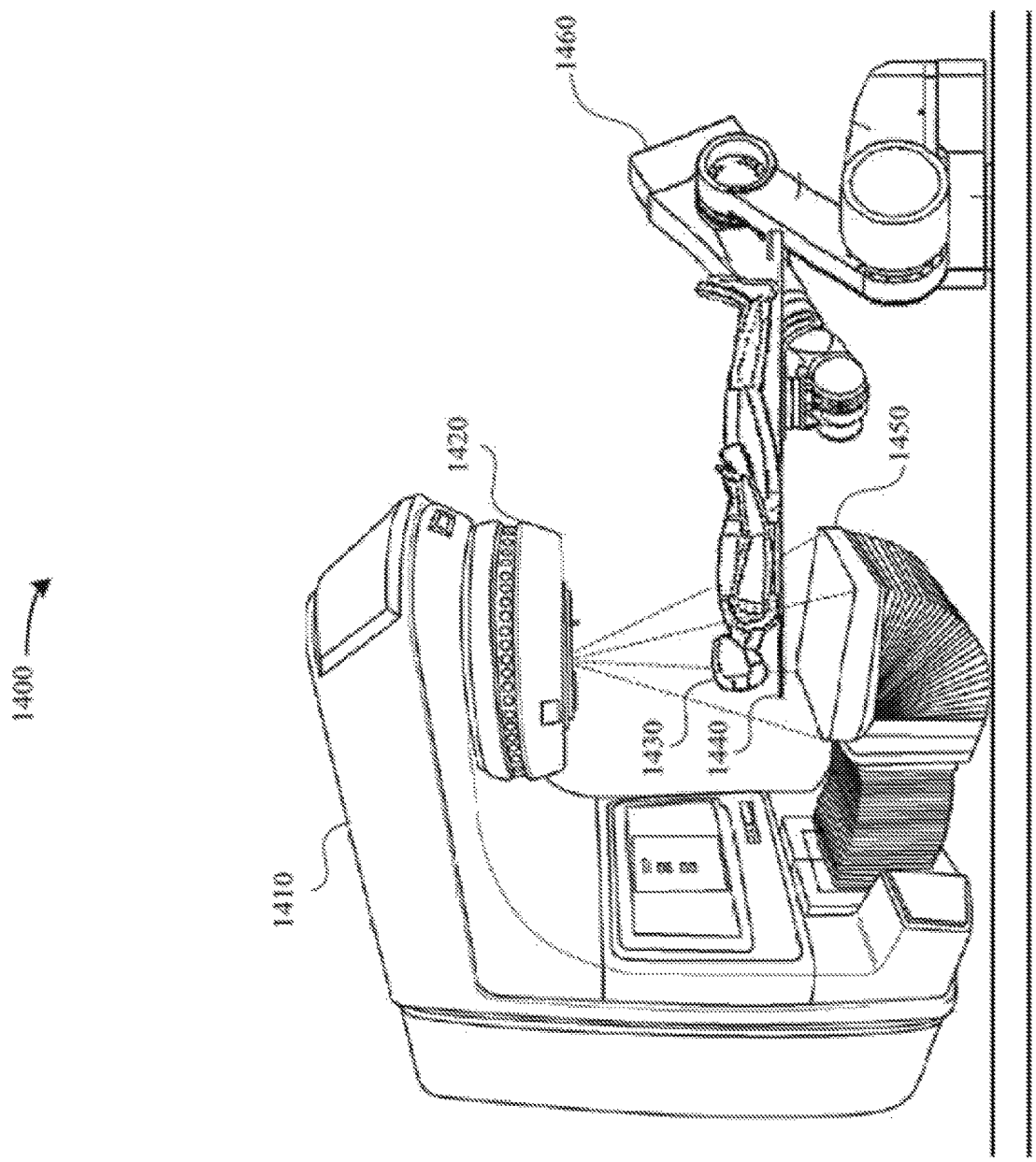

FIELD REPLACEABLE, DISPOSABLE, AND THERMALLY OPTIMIZED X-RAY TARGET WITH INTEGRAL BEAM CURRENT MONITORING

TECHNICAL FIELD

The present disclosure relates to a field replaceable, disposable, and thermally optimized X-ray target with integral beam current monitoring.

BACKGROUND

Accelerator-based radiation therapy typically generates a high energy X-ray beam via bremsstrahlung ("braking radiation"). A relativistic electron beam is incident on a target material of high atomic number ("high Z"). The electrons are deflected, and thus accelerated, by electromagnetic interactions with nuclei of the target material, causing emission of high energy photons. Some of these photons have enough energy to create electron-positron pairs, which then interact with nuclei of the target material to emit more photons. The result is an "electromagnetic shower" or "electromagnetic cascade" of electrons, positrons, and photons. Any electrons which escape the target are typically eliminated from the therapy beam by an electron absorber made of material with low atomic mass.

BRIEF DESCRIPTION OF THE DRAWINGS

The present disclosure will be understood more fully from the detailed description given below and from the accompanying drawings of various implementations of the disclosure.

FIG. 1C illustrates a c-arm gantry-based radiation treatment system, in accordance with embodiments described herein.

DETAILED DESCRIPTION

Described herein are embodiments of methods and apparatus for a field replaceable, disposable, and thermally optimized X-ray target with integral beam current monitoring. In various embodiments, an X-ray target and X-ray target assembly may be attached externally to a linear accelerator ("LINAC") housing outside a vacuum envelope of the LINAC. Traditional X-ray targets of a LINAC are integrated within the vacuum of the LINAC and are therefore not separately replaceable. Upon breakdown of the X-ray target, the entire LINAC may require maintenance to replace the target, which may result in long downtime of the LINAC causing significant costs to the operator and/or owner of the machine. Furthermore, the time at which the target fails may be unpredictable and thus planning for the maintenance discussed above may be difficult.

Advantageously, the embodiments described herein provide a field replaceable, disposable, and thermally optimized X-ray target with integral beam current monitoring. The X-ray target material may be attached to a target holder assembly that can then be attached externally to a LINAC outside the vacuum envelope. The target holder assembly may therefore be attached and detached to the LINAC without significant maintenance to the LINAC and without losing vacuum. Accordingly, upon failure of a current X-ray target, the target holder assembly of the failed target may quickly be removed and replaced with a new target holder assembly having a new target material without significant downtime. Additionally, the target holder assembly may include cooling channels that provide larger coolant to surface cross sectional contact to increase heat removal during use of the X-ray target. Because high temperatures in the target material can cause degradation of the target, the increased heat removal may extend the lifetime of the target. Finally, the target and target holder assembly may include a toroidal current transformer and/or be electrically isolated from the LINAC providing for the ability to directly measure X-ray beam current.

Figure 1A:
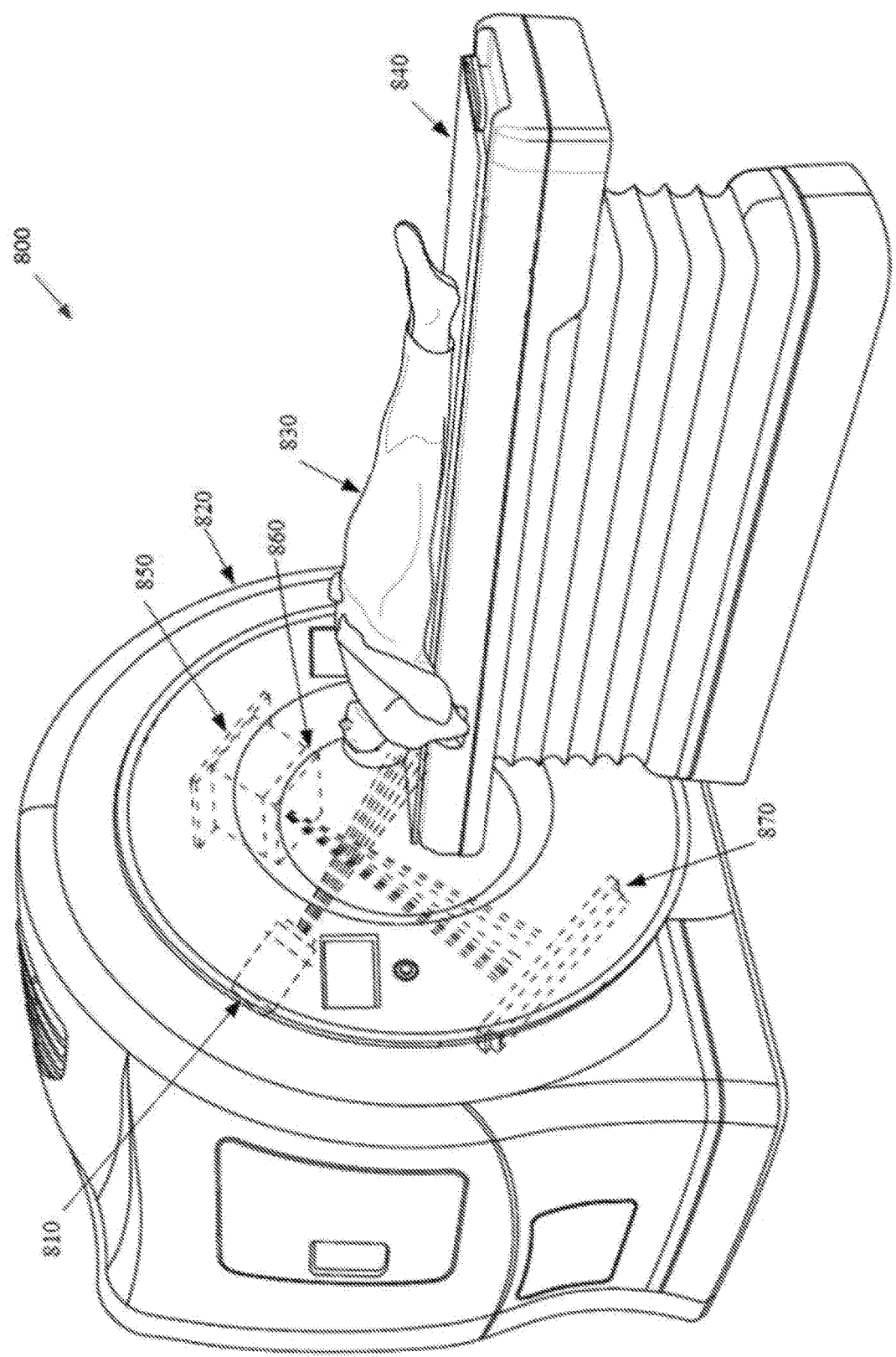
FIG. 1A illustrates a helical radiation delivery system, in accordance with embodiments described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multi-leaf collimator (MLC) 860. The MLC includes a housing that houses multiple leaves that are movable to adjust an aperture of the MLC to enable shaping of the treatment beam. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
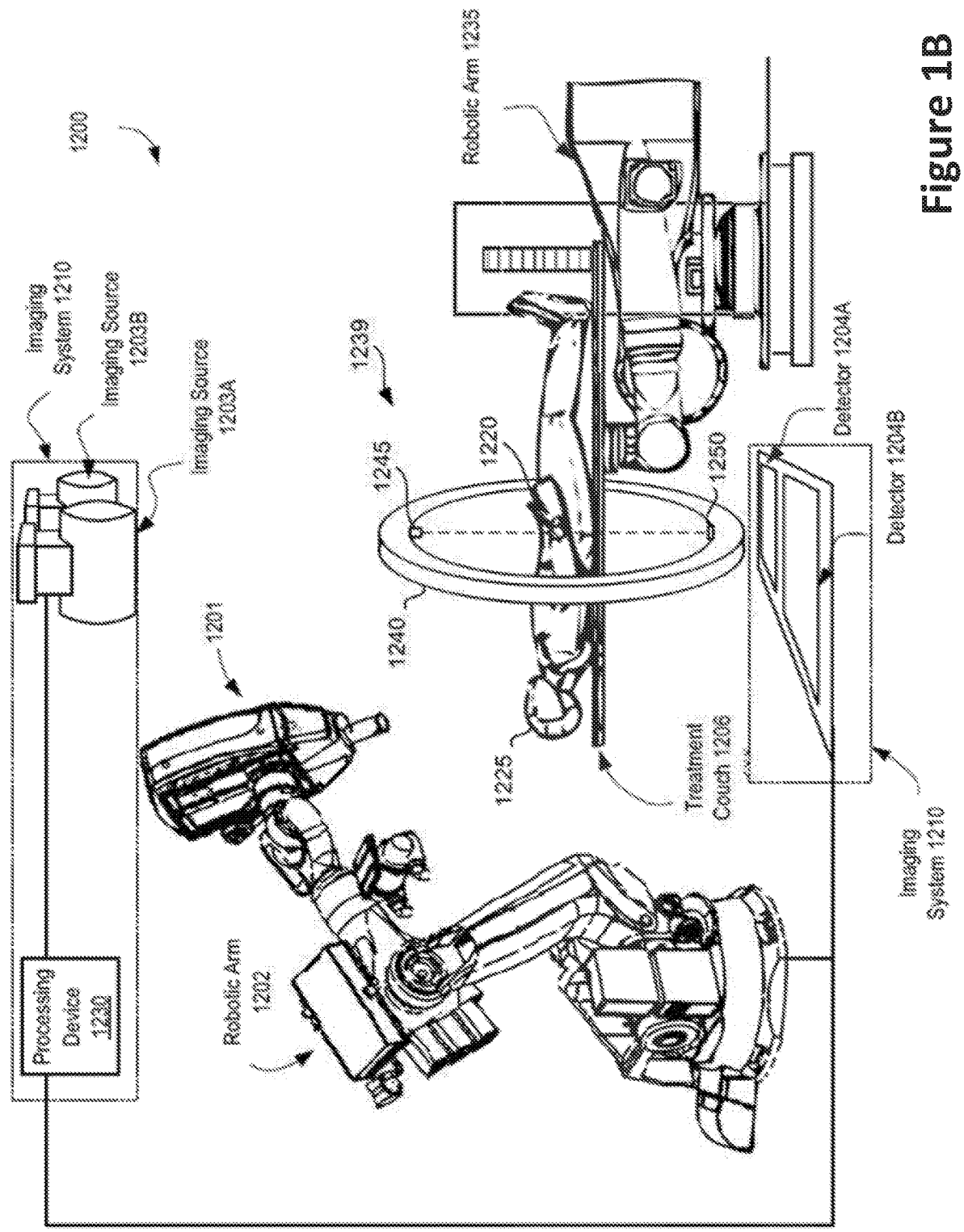
FIG. 1B illustrates a radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 in mounted in front of the LINAC to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

FIG. 1C. Illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a gantry 1410, a LINAC 1420, an MLC 1470 in front of the LINAC 1420 to shape the beam, and a portal imaging detector 1450. The gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2:
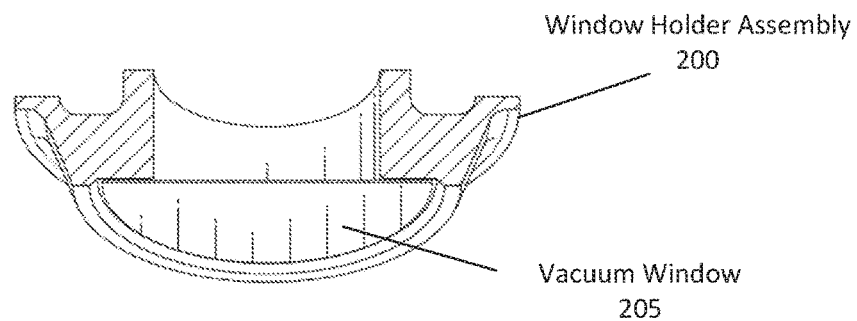
FIG. 2 illustrates an example window holder assembly to be attached to an output of a LINAC, in accordance with embodiments described herein.

FIG. 2 illustrates an example window holder assembly 200 to be attached to an output of a LINAC, in accordance with embodiments of the disclosure. In one embodiment, the window holder assembly 200 may be made of copper. The window holder assembly 200 may include a vacuum window 205 attached to the window holder assembly 200. For example, the vacuum window 205 may be attached using hermetic welding, laser welding, brazing, or any other suitable process. The vacuum window 205 may be made of beryllium, stainless steel, titanium, or any other suitable material with low atomic mass. The window holder assembly 200 may be attached directly to the LINAC at the output of the LINAC. For example, the window holder assembly 200 may be welded to the LINAC to ensure that the LINAC can sustain an internal vacuum environment. The target holder assembly 200 may align directly with a protective window and x-ray target of a target holder assembly, as described with respect to FIG. 3 below.

Figure 3:
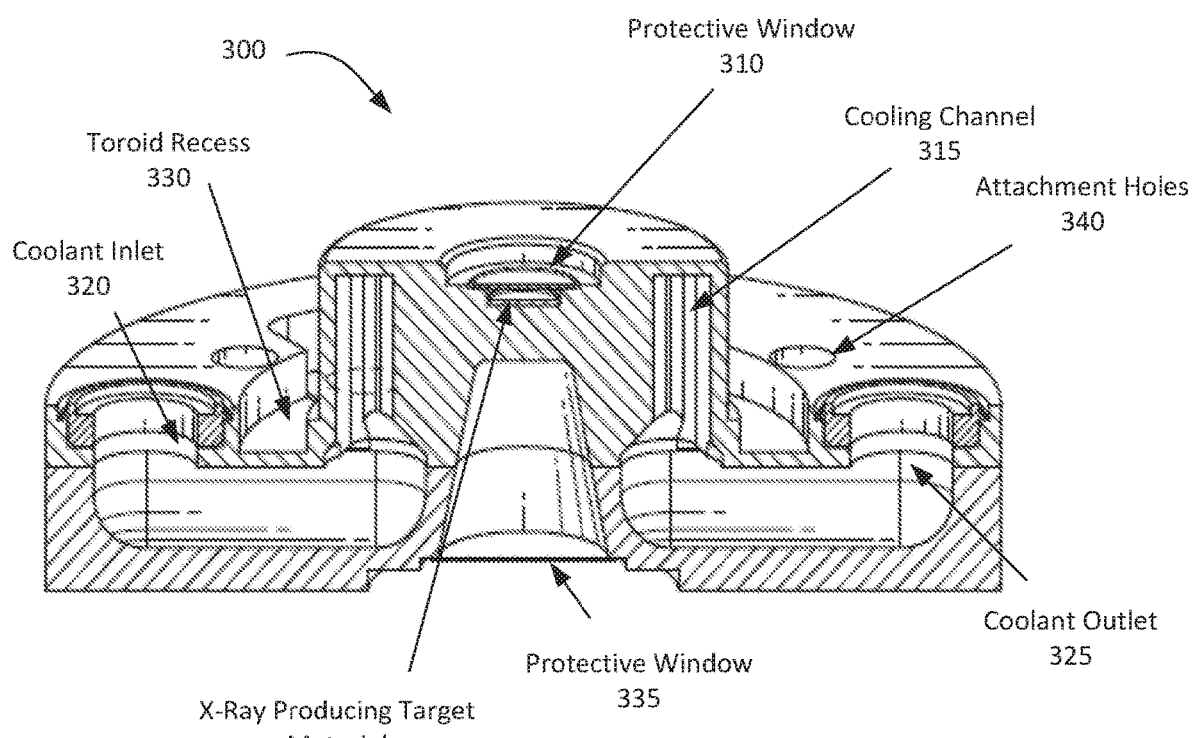
FIG. 3 illustrates a cross sectional view of an example field replaceable, disposable, and thermally optimized X-ray target holder assembly with integral beam current monitoring, in accordance with embodiments described herein.
Figure 4:
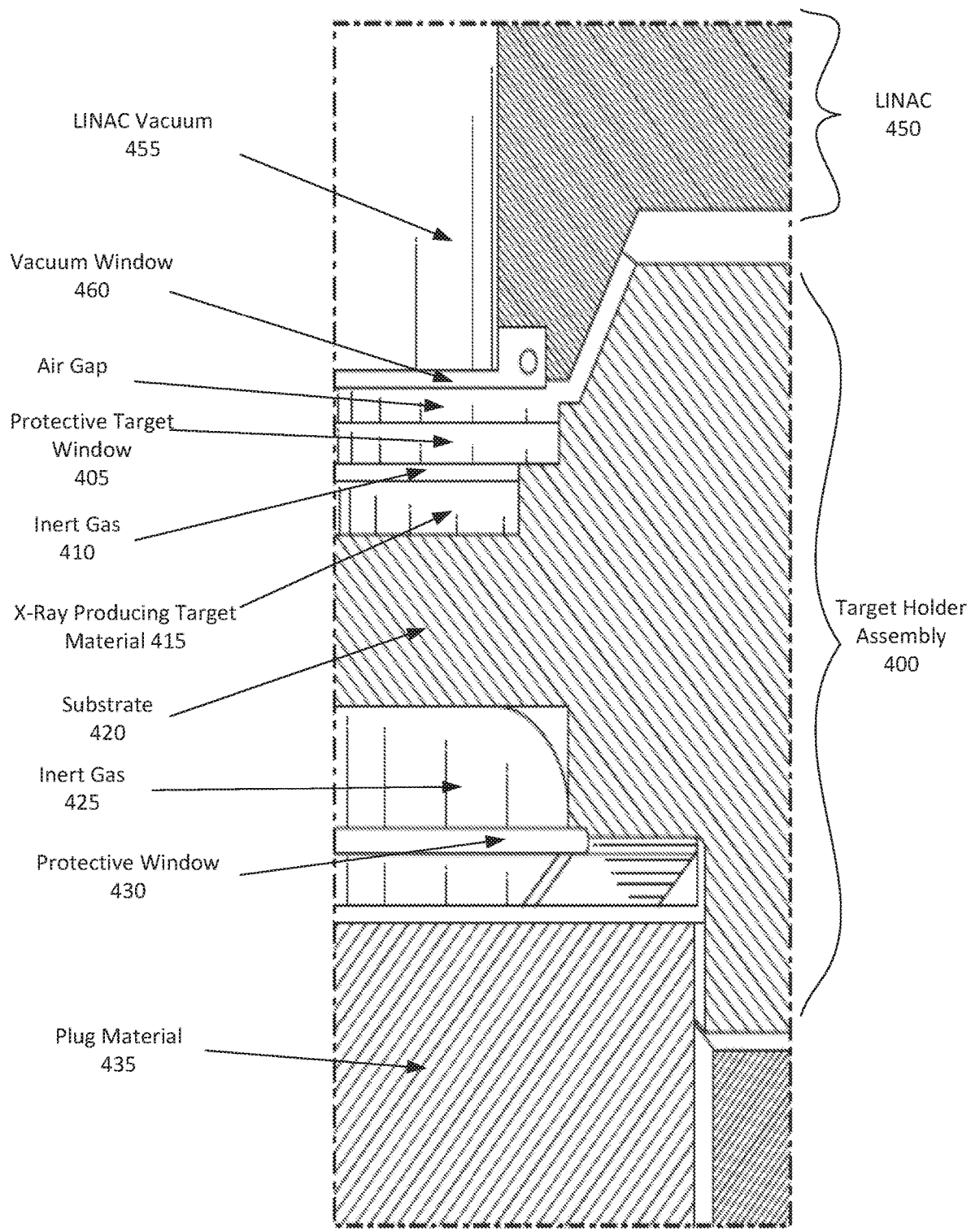
FIG. 4 illustrates an example of a field replaceable, disposable, and thermally optimized X-ray target with integral beam current monitoring as attached to a LINAC, in accordance with embodiments described herein.

FIG. 3 illustrates a cross sectional view of an example field replaceable, disposable, and thermally optimized X-ray target holder assembly with integral beam current monitoring, in accordance with embodiments of the disclosure. As depicted in FIG. 3, the target holder assembly 300 may include an x-ray producing target material 305 protected by a protective window 310. The target holder assembly 300 may be structured with a recess to allow the protective window 310 to be in close proximity (e.g., within 1 mm) to the vacuum window 205 of the window holder assembly 200, depicted in FIG. 2. When the target holder assembly is attached to the LINAC, a very small air gap (e.g., less than 1 mm) may be left between the vacuum window 205 and the protective window 310 over the x-ray producing target material 305 of the target holder assembly 300, as depicted in FIG. 4 discussed below. The x-ray producing target material 305 may be tungsten, uranium, gold, or other material with a high atomic mass (e.g., higher than 40).

Dimensions of the x-ray producing target material 305 are discussed below with respect to FIG. 4. The target holder assembly 300 may also include a set of attachment holes 340 to bolt the target holder assembly to the housing of the LINAC. Other attachment/coupling means may also be used, such as clamps, welding, or the like. The target holder assembly 300 may be attached to a LINAC as described in any one of FIGS. 1A-C.

In one embodiment, the target holder assembly 300 includes a cooling channel 315 around the circumference of the target area. In embodiments, the cooling channel 315 may include a complex geometry to increase the surface area of the target holder assembly 300 that is in contact with a coolant flowing through the cooling channel. In one example, the geometry of the cooling channel 315 provide for at least 1.5 times coolant path length than a circular channel around the target area. In one example, the coolant may be water, or other refrigerant type cooling liquid with high specific heat capacity (e.g., greater than 1). The cooling liquid may be received at a coolant inlet 320 of the target assembly 300 and returned via a coolant outlet 325 of the target assembly. In one embodiment, the coolant inlet 320 and coolant outlet 325 are integrally coupled to the LINAC and receive the coolant from and return the coolant to the LINAC directly. The coolant inlet 320 and the coolant outlet 325 may be coupled to the LINAC via a water tight seal. For example, metallic C-rings may be used to provide the watertight seal at the coolant inlet 320 and the coolant outlet 325. Alternatively, the coolant inlet 320 may receive a coolant and coolant outlet 325 may return the coolant via externally routed coolant lines.

In one embodiment, the target holder assembly 300 may include a toroid recess 330. The toroid recess may be dimensioned to receive a toroidal current transformer or other current transformer to measure a current of the electron beam received at the x-ray generating target material 305. Utilizing a toroidal current transformer may allow the beam current to be measured even when electrically grounded to the LINAC itself (e.g., not electrically insulated from the LINAC). In one example, the measured current may be on the scale of 100-300 mA with a pulse width of 2 to 6 micro-seconds. The current transformer may also measure a shape of the current pulse. To measure beam current, the toroidal current transformer may include conducing wire wrapped around an insulator core. For example, the toroidal current transformer may include 10-60 turns (e.g., wrapped around the core 10-60 times) depending on the size of the toroid core and the wire used. In one example, the wire may be a magnet wire. The toroidal current transformer may be made to any dimension that allows the toroidal current transformer to be included on the target holder assembly 300. For example, the inner diameter of the toroid may be between 20 mm and 40 mm and the outer diameter may be between 25 and 55 mm. However, any appropriate dimensions may be used that will fit within the toroid recess 330. The measured currents and pulse shape may be used for calibration or diagnostics of the LINAC, energy servo control, or other optimizations.

In an embodiment, the x-ray producing target material 305 may be electrically isolated from the LINAC. For example, the target holder assembly 300 may be made of an insulator such as ceramic. In another embodiment, the target holder assembly 300 may be coated with an electrically neutral coating to provide electrical isolation from the LINAC. The current may be measured across a resistor connected to the x-ray producing target material 305 and grounded on the other end. As described above, the current and shape of the current may be measured and the measurements may be used for any number of LINAC optimizations.

In one embodiment, the target holder assembly 300 may include another protective window 335 at an exit of the target holder assembly 300. The protective window 335 may be made of a material with low atomic mass. For example, the protective window 335 may be made of beryllium, stainless steel, titanium, or any other suitable material with low atomic mass. The exit of the target holder assembly may be a cylindrical or conical shaped recess in the target holder assembly 300. The protective window 335 may enclose an inert gas atmosphere in the recess. For example, the inert gas atmosphere may be argon, hydrogen, vacuum, or other low oxidizing atmosphere. The inert gas atmosphere may prevent additional wear with the cavity due to oxidation. The protective window 335 may be welded to the target holder assembly 300. For example, the protective window 335 may be welded using hermetic welding, laser welding, brazing, or any other suitable process.

Figure 5A:
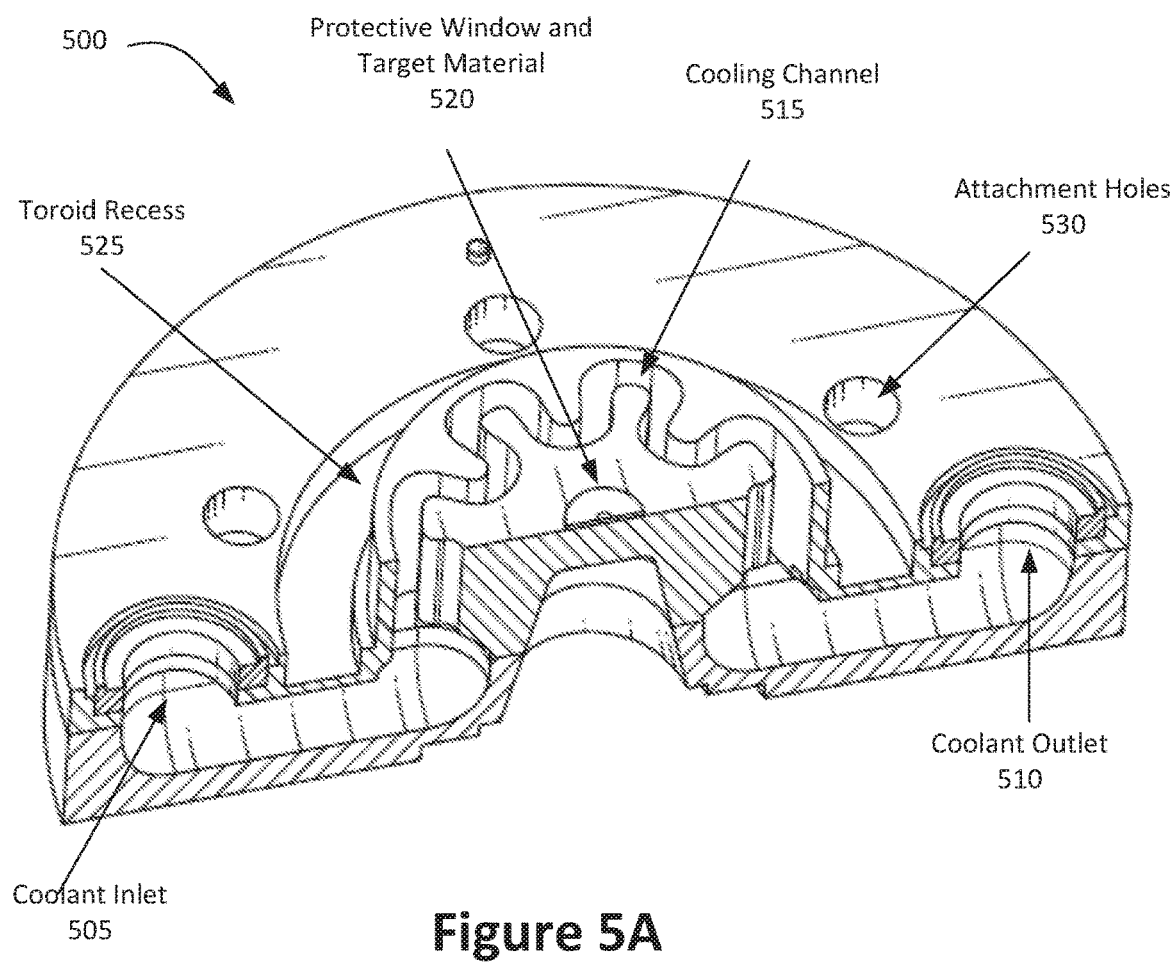
FIGS. 5A-D illustrate an example embodiment of a field replaceable target assembly, in accordance with embodiments described herein.
Figure 5B:
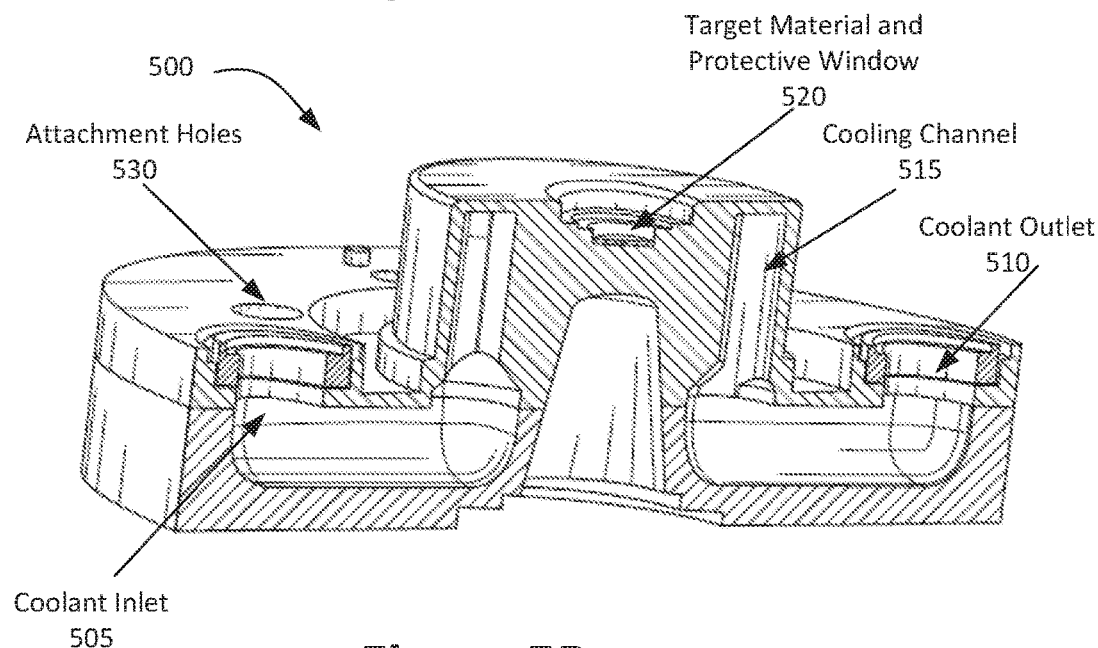
Figure 5C:
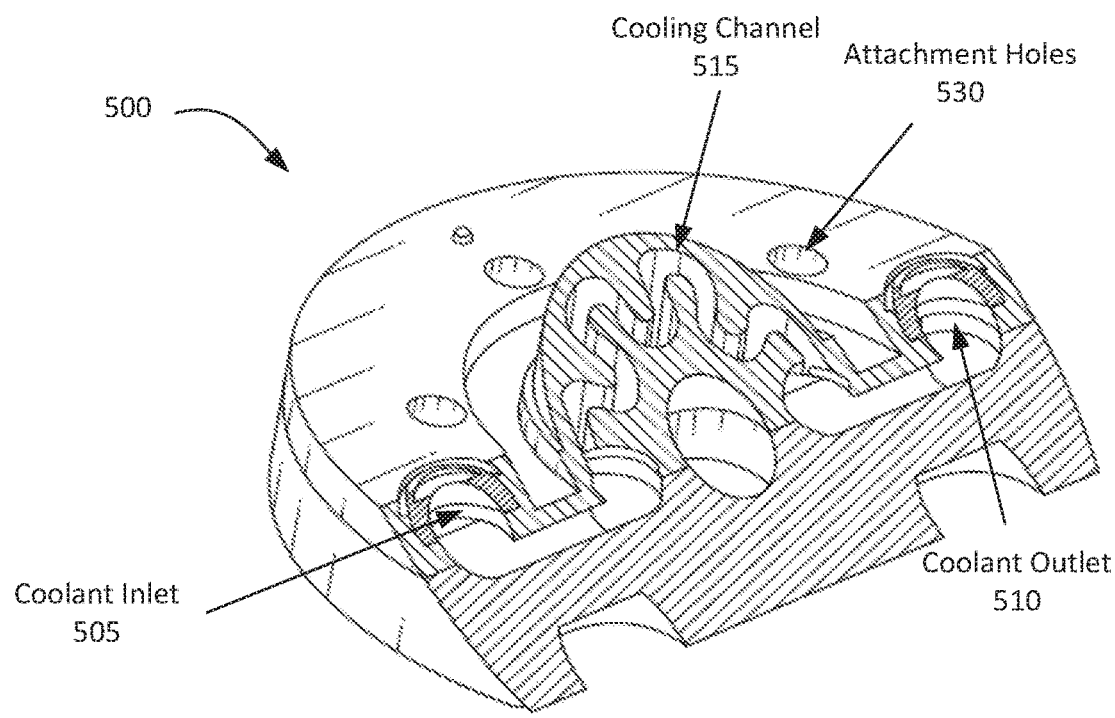
Figure 5D:
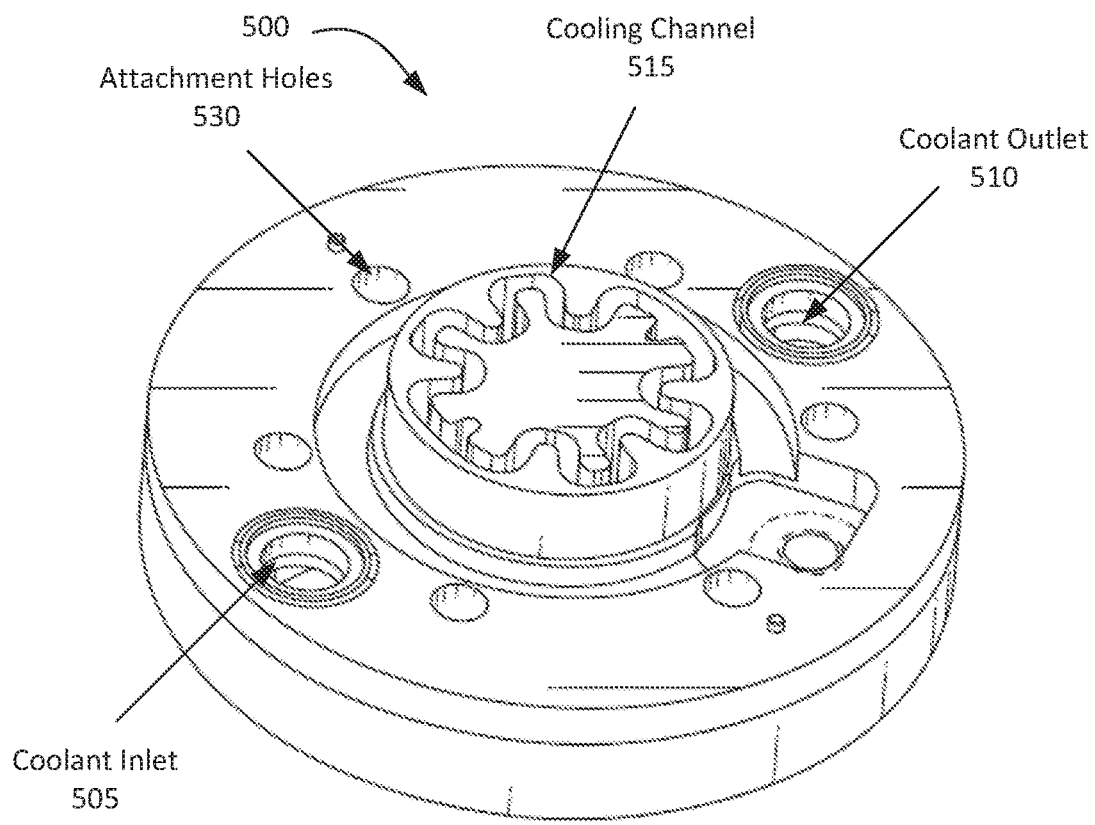

FIG. 4. illustrates an example of a field replaceable, disposable, and thermally optimized X-ray target with integral beam current monitoring as attached to a LINAC, in accordance with embodiments of the disclosure. As depicted, a target holder assembly 400 is attached directly to a LINAC 450. The LINAC may hold an internal vacuum 455 in which electrons are accelerated via electromagnetic waves. A window holder assembly, described in more detail below with respect to FIG. 5A, may be attached to the output of the LINAC 450. For example, the window holder assembly may be welded to the output of the LINAC 450. The window holder assembly may include a vacuum window 460 made of a material with a low atomic mass to keep the LINAC 450 in vacuum and to allow an electron beam to pass through relatively unimpeded. The target holder assembly 400 may include an x-ray target material 415 securely attached to the target holder assembly 400. A protective window 405 may be attached to the target holder assembly 400 above the x-ray target material 415. Sealed between the x-ray target material 415 and the protective window 405 may be an inert non-oxidizing gas atmosphere 410 to protect the target material 415 from the effects of oxidation. For example, the inert gas atmosphere may be argon, hydrogen, vacuum, or other low oxidizing atmosphere. In some embodiments, the inert gas 410 may be produced by the welding or brazing techniques used to attach the protective target window 405.

The thickness for the x-ray target material 415, the protective windows 405, 430, and the substrate 420 may be expressed in terms of radiation length. Radiation length is the mean distance over which a high-energy electron loses all but 1/e of its energy by bremsstrahlung interactions. Therefore, radiation length is an inherent property of the target material (e.g., the atomic mass of the target material). Generally, a larger atomic mass will reduce the corresponding radiation length. Furthermore, the actual measure thickness for a radiation length of the target material may vary from material to material. For example, the radiation length of tungsten is approximately 3.5 mm and the radiation length of gold is 3.34 mm. In one embodiment, the target material is between 0.01 and 0.2 radiation lengths for tungsten in thickness. Therefore, a target material of tungsten may have a thickness of 0.035 mm to 0.7 mm while a target material of gold may have a thickness of 0.033 mm to 0.67 mm. Similarly, any other target material used may have a thickness between 0.01 and 0.2 radiation lengths but may vary in actual thickness according to the radiation length of the material used.

In another embodiment, the target material may be between 0.25 and 2 radiation lengths for tungsten in thickness. Therefore, a target material of tungsten may have a thickness of 0.9 mm to 7 mm while a target material of gold may have a thickness of 0.8 mm to 6.7 mm. Similarly, any other target material used may have a thickness between 0.25 and 2 radiation lengths but vary in actual thickness according to the radiation length of the material used.

In one embodiment, the protective windows may be thin with respect to the radiation length for the material (e.g., a thin foil) and may have a low atomic mass (e.g., less than 30). For example, the windows may be made of beryllium, titanium, stainless steel, carbon foil or other similar materials. In one example, the material may have a thickness on a scale of $10^{-5}$ radiation lengths (e.g., between 0.025-0.075 mm for Beryllium, 0.0025-0.0075 mm for titanium, and 0.014-0.42 mm for carbon foil) so that the electrons pass through relatively unimpeded.

The substrate 420 may be a thickness that stops any excess electrons from the electron beam generated by the LINAC 450 from exiting the LINAC 450 and target assembly 500. However, the substrate 420 may also be thin enough and have a low atomic mass to allow the x-rays produced by the x-ray target to pass through relatively unimpeded. In one example, the substrate 420 is made of copper and has a thickness of at least 0.1 radiation lengths (i.e., at least 1.4 mm).

The vacuum window 455 at the output of the LINAC and the protective target window 405 may be directly aligned to allow an electron beam to pass through to the target material 415. The target holder assembly 400 may further include a substrate 420 directly beneath the target material 415. The substrate 420 may be comprised of copper or other material of low atomic mass (e.g., less than 30) and may be thick enough to prevent any excess electrons from the electron beam of the LINAC 450 from passing through while being thin enough to allow x-ray radiation to pass through. Additionally, below the substrate 420 may be an exit cavity that is a hollowed out conical structure of the target holder assembly 400. The exit cavity may direct the radiation produced by the target material 415 in the intended direction for treatment. Another protective window 430 may be attached at the opening of the exit cavity with another non-oxidizing gas 425 atmosphere trapped within to prevent additional wear on the target holder assembly 400 due to oxidation. For example, the inert gas atmosphere may be argon, hydrogen, vacuum, or other low oxidizing atmosphere. In one example, the target holder assembly 500 includes a plug material 435, such as aluminum, to stop any excess electrons from exiting the target holder assembly 400 with the x-ray treatment beam.

FIGS. 5A-D illustrate an example embodiment of a field replaceable target assembly. The target assembly 500 may include a coolant inlet 505 and a coolant outlet 510. The coolant inlet and outlet may be coupled to a cooling channel 515 through which a cooling liquid may flow to extract heat from the x-ray target 520 and substrate. The target assembly 500 may further include one or more attachment holes 530 for receiving bolts to attach the target assembly 500 to a LINAC. In an embodiment, the target assembly 500 may not include attachment holes 530 and may instead be attached by alternative means, such as a clamp, welding, etc.

The coolant inlet 505 and coolant outlet 510 may each include sealing inserts to provide a water-tight seal for a liquid coolant to flow from the LINAC to the coolant inlet 505 and from the coolant outlet 510 back to the LINAC. The coolant may flow through the cooling channel 515 that directs the coolant around the circumference of the x-ray target 520. As depicted, the cooling channel 515 may be a serpentine shape around the x-ray target 520. The serpentine shape may increase the surface area of the coolant that is in contact with a conductive substrate surrounding the target 520 and therefore increase the heat transfer from the conductive substrate to the coolant. Furthermore, the serpentine channel may provide fin-like structures that act as a heat sink to draw heat from the target 520 to the coolant flowing through the cooling channel 515. In some embodiments, the target assembly 500 is integrally attached to a LINAC and receives a coolant at the coolant inlet 505 from the LINAC and then returns the heated coolant back to the LINAC via the coolant outlet 510.

The cooling channel 515 may have a high aspect ratio of height to width (e.g., the cooling channel 515 may be tall and skinny to provide a large surface area for heat transfer to the coolant from the contact surface. In embodiments, the cooling channel 515 may include rifling and/or screw to cause turbulence in the flow of the coolant. In embodiments, the cooling channel 515 may be any complex geometry to increase the coolant path to up to and more than 1.5 times the length of a circular channel.

Finally, the target assembly 500 may include a recess 210 for a pulse toroid. For example, a pulse toroid may be disposed within the recess 210 and may detect a pulse current received at the x-ray target 220 from the LINAC. In another embodiment, a mounting surface of the x-ray target 220 and the interior of the cooling channels may be coated with a material of high electrical resistivity (i.e., an insulator such as Diamond-like Carbon). The coating may provide electrical isolation of the target 220. The target may further be in contact with a grounded surface of the LINAC. Therefore, current can be measured between the target 220 and ground. Thus, the beam current may be directly and precisely measured.

The target holder assembly 500 may include an exit cavity directly beneath the substrate on which the target material 520 is attached. The exit cavity may be enclosed by another protective window. The enclose part of the exit cavity may include a non-oxidizing inert gas atmosphere to prevent damage due to oxidation.

Figure 6:
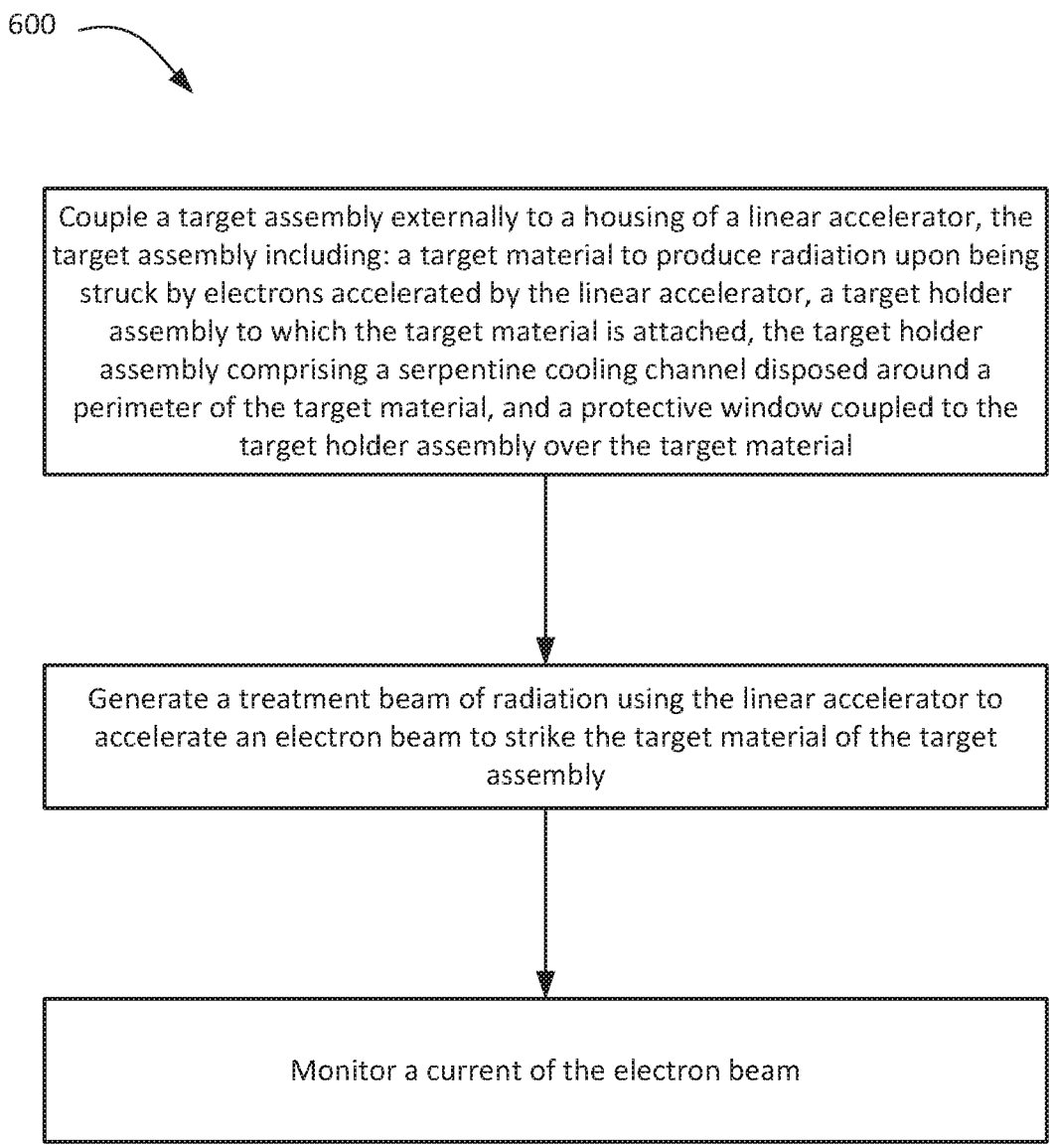
FIG. 6 illustrates an example method of using a field replaceable, disposable, and thermally optimized X-ray target with integral beam current monitoring, in accordance with embodiments described herein.

FIG. 6 illustrates an example method of using a field replaceable, disposable, and thermally optimized X-ray target with integral beam current monitoring. With reference to FIG. 6, method 600 illustrates example functions used by various embodiments. Although specific function blocks ("blocks") are disclosed in method 600, such blocks are examples. That is, embodiments are well suited to performing various other blocks or variations of the blocks recited in method 600. It is appreciated that the blocks in method 600 may be performed in an order different than presented, and that not all of the blocks in method 600 may be performed.

The method begins at block 602, where a target assembly is coupled externally to a housing of a linear accelerator. The target assembly may include a target material to produce radiation upon being struck by electrons accelerated by the linear accelerator, a target holder assembly to which the target material is attached, the target holder assembly comprising a serpentine cooling channel disposed around a perimeter of the target material, and a protective window coupled to the target holder assembly over the target material. In one example, when the target holder assembly is attached to the linear accelerator the protective window coupled to the target holder assembly is aligned with a vacuum window at an output of the linear accelerator.

At block 604, a treatment beam of radiation is generated using the linear accelerator to accelerate an electron beam to strike the target material of the target assembly. At block 606, a current of the electron beam is monitored. In one example, the current is monitored by electrically isolating the target material and directly measuring an electric current at the target material. In another example, the current is monitored by a toroidal current transformer disposed in the target holder assembly. It should be noted that method 600 can be performed in association with any of the description and/or embodiments discussed above with respect to FIGS. 1-5D.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense. Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A linear accelerator target apparatus, comprising:
   a target material to produce radiation upon being struck by electrons accelerated by a linear accelerator;
   a target holder assembly to which the target material is attached, the target holder assembly comprising a cooling channel disposed around a perimeter of the target material, and wherein the target holder assembly is configured to be detachably coupled to a housing of the linear accelerator;
   a protective window coupled to the target holder assembly over the target material;
   at least one coupling interface between the cooling channel and the linear accelerator, and wherein the cooling channel comprises a serpentine shaped cooling channel.

2. The apparatus of claim 1, further comprising:
   a toroidal current transformer coupled to the target holder assembly, the toroidal current transformer to measure an electron beam current of the linear accelerator.

3. The apparatus of claim 1, wherein the target holder assembly further comprises:
   a current sensing component coupled to the target material to measure an electron beam current of the linear accelerator, and wherein the target material is electrically isolated from the linear accelerator.

4. The apparatus of claim 1, wherein the target material is less than 0.2 radiation lengths in thickness with respect to an atomic mass of the target material and an energy of the electrons.

5. The apparatus of claim 1, further comprising:
   an inert gas atmosphere disposed between the protective window and the target material.

6. The apparatus of claim 1, wherein the protective window is comprised of beryllium.

7. The apparatus of claim 1, wherein the target holder assembly is coupled externally to the linear accelerator, and wherein the linear accelerator comprises a vacuum window at an output of the linear accelerator.

8. The apparatus of claim 7, wherein when the target holder assembly is coupled to the linear accelerator, the protective window coupled to the target holder assembly is aligned with a second protective window at the output of the linear accelerator.

9. A radiation delivery system, comprising:
   a linear accelerator;
   a target material to produce radiation upon being struck by electrons accelerated by the linear accelerator;
   a target holder assembly to which the target material is attached, the target holder assembly comprising a cooling channel disposed around a perimeter of the target material, and wherein the target holder assembly is configured to be detachably coupled to a housing of the linear accelerator;
   a protective window coupled to the target holder assembly over the target material; and
   at least one coupling interface between the cooling channel and the linear accelerator, and wherein the cooling channel comprises a serpentine shaped cooling channel.

10. The system of claim 9, further comprising:
    a toroidal current transformer coupled to the target holder assembly, the toroidal current transformer to measure an electron beam current of the linear accelerator.

11. The system of claim 9, wherein the target holder assembly further comprises:
    a current sensing component coupled to the target material to measure an electron beam current of the linear accelerator, and wherein the target material is electrically isolated from the linear accelerator.

12. The system of claim 9, wherein the target material is less than 0.2 radiation lengths in thickness with respect to an atomic mass of the target material and an energy of the electrons.

13. The system of claim 9, further comprising:
    an inert gas atmosphere disposed between the protective window and the target material.

14. The system of claim 9, wherein the protective window is comprised of beryllium.

15. The system of claim 9, wherein the target holder assembly is coupled externally to the linear accelerator, and wherein the linear accelerator comprises a vacuum window at an output of the linear accelerator.

16. The system of claim 15, wherein when the target holder assembly is attached to the linear accelerator, the protective window coupled to the target holder assembly is aligned with a second protective window at the output of the linear accelerator.

17. A method comprising:
    coupling a target assembly externally to a housing of a linear accelerator, the target assembly comprising:
      a target material to produce radiation upon being struck by electrons accelerated by the linear accelerator;
      a target holder assembly to which the target material is attached, the target holder assembly comprising a serpentine cooling channel disposed around a perimeter of the target material, and
      a protective window coupled to the target holder assembly over the target material; and
    generating a treatment beam of radiation using the linear accelerator to accelerate an electron beam to strike the target material of the target assembly.

18. The method of claim 17, further comprising:
    monitoring a current of the electron beam using a toroidal current transformer disposed in the target holder assembly.

19. The method of claim 17, further comprising:
monitoring a current of the electron beam by electrically isolating the target material and directly measuring an electric current at the target material.

20. The method of claim 17, wherein when the target holder assembly is attached to the linear accelerator, the protective window coupled to the target holder assembly is aligned with a vacuum window at an output of the linear accelerator.

\* \* \* \* \*